United States Patent [19]
Kudo et al.

[11] Patent Number: 5,661,011
[45] Date of Patent: Aug. 26, 1997

[54] SEXING METHOD OF BOVINE EMBRYOS

[75] Inventors: Toshiyuki Kudo; Yoshiaki Itagaki; Seiji Sato; Shizuyo Sutou; Toyoo Nakamura, all of Ibaraki, Japan

[73] Assignee: Itoham Foods, Inc., Japan

[21] Appl. No.: 458,393

[22] Filed: Jun. 2, 1995

Related U.S. Application Data

[62] Division of Ser. No. 984,044, Dec. 2, 1992, Pat. No. 5,461,145.

[30] Foreign Application Priority Data

Dec. 13, 1991 [JP] Japan ................... 3-352032

[51] Int. Cl.$^6$ .................................. C12P 19/34
[52] U.S. Cl. ................ 435/91.2; 536/24.33; 536/24.31
[58] Field of Search ............... 435/91.2; 536/24.33, 536/24.31

[56] References Cited

U.S. PATENT DOCUMENTS 4,960,690  10/1990  Ellis et al. .
5,055,393  10/1991  Kwoh et al. .

FOREIGN PATENT DOCUMENTS

WO86/07095  12/1986  WIPO ................. C12Q 1/68
WO89/01978   3/1989  WIPO ................. C12Q 1/68
WO89/07154   8/1989  WIPO ................. C12Q 1/68
WO91/00365   1/1991  WIPO ................. C12Q 1/68

OTHER PUBLICATIONS

Anderson et al., 1982, "Complete Sequence of Bovine Mitochondrial DNA, Conserved Features of the Mammalian Mitochondrial Genome," *J. Mol. Biol.* 156:683–717.

Ellis et al., 1988, "Sex Determination of Bovine Embryos Using Male–Specific DNA Probes," *Theriogenology* 29(1):242.

European Search Report, Mar. 19, 1993.

Anderson et al., 1982,, "Complete Sequence of Bovine Mitochondrial DNA, Conserved Features of the Mammalian Mitochondrial Genome," *J. Mol. Biol.* 156:683–717.

Bondioli et al. (1989) "The Use of Male–Specific Chromosomal DNA Fragments to Determine the Sex of Bovine Preimplantation Embryos", *Theriogenology* vol. 31:95–104.

*Primary Examiner*—Kenneth R. Horlick
*Assistant Examiner*—Joyce Tung
*Attorney, Agent, or Firm*—Pennie & Edmonds

[57] ABSTRACT

The present invention provides PCR primers with which sexing of bovine embryos can be easily attained and provides a practical, rapid and reliable method for determining the sex of bovine embryos using these primers. The methods for determining the sex of the bovine embryos are characterized by discriminating PCR products which are obtained by amplifying specific DNA sequences by PCR with pairs of male-specific and gender-neutral primers. These primers are derived from DNAs which specifically hybridize to the bovine male genome and from DNAs which gender-neutrally hybridize to both bovine male and female genomes.

16 Claims, 11 Drawing Sheets

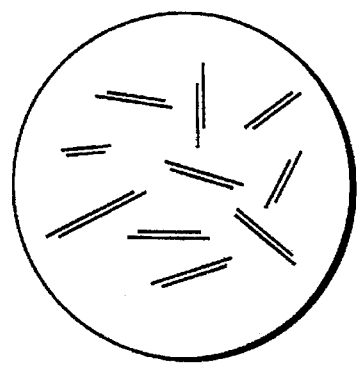
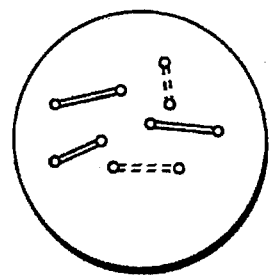
FIG. 1a  FIG. 1b
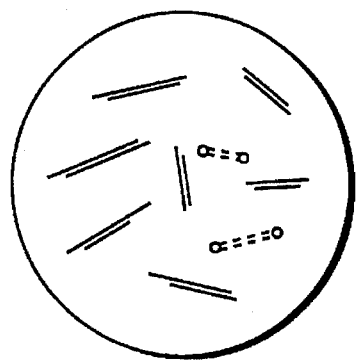
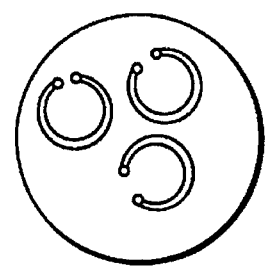
FIG. 1c  FIG. 1d
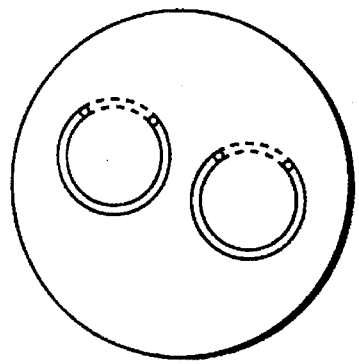
FIG. 1e

SEXING METHOD OF BOVINE EMBRYOS

This is a division of application Ser. No. 07/984,044, filed Dec. 2, 1992, U.S. Pat. No. 5,461,145.

1. FIELD OF THE INVENTION

The present invention relates to the method of sexing of bovine embryos and DNA primers for this method.

2. BACKGROUND OF THE INVENTION

The development of modern biotechnology has made artificial insemination a common technique in industrial animals. In particular, artificial insemination with frozen sperm has been established in cattle. Although sexing is an important technique from the industrial viewpoint, a simple and reliable experimental method has been rather difficult to develop in the field of cattle biotechnology.

The following methods have so far been tried in order to sex bovine embryos experimentally.

2.1 Separation and Identification of Y-bearing Spermatozoa

Since females are homozygotic and males are heterozygotic in mammals, including cattle, eggs are sexually homogeneous and spermatozoa consist of two populations. That is, ova fused with Y-bearing spermatozoa become male embryos and ova fused with X-bearing spermatozoa become female embryos. Therefore, if X- and Y-bearing spermatozoa can be separated, female and male embryos can be produced as desired. The following methods have been tried in order to separate X- and Y-bearing spermatozoa.

2.1.1 Separation by Sedimentation Method Utilizing Gravity Force or by Centrifugation in Density Gradients The X-chromosome comprises approximately 5% of the genome, and the Y-chromosome comprises approximately 3%. This slight difference implies that light spermatozoa are Y-bearing and heavy ones are X-bearing. However, definite separation of X-bearing spermatozoa from Y-bearing spermatozoa is difficult, because the weight difference between X- and Y-bearing spermatozoa, as measured by gravity force is small; the size of spermatozoa naturally fluctuates; and the specific gravity of spermatozoa depends to some extent on the degree of maturity.

2.1.2 Separation by Electrophoresis

Separation by electrophoresis is based on the premise that there is a difference in surface charges between X- and Y-bearing spermatozoa. Generally, charges on the cytoplasmic membrane depend on the amount of sialic acid bound to glycoproteins. During meiosis, however, four spermatids covered by the Sertoli cell are open to each other through cytoplasmic bridges and therefore they form a kind of syncytium. This means that differences in surface charges between X- and Y-bearing spermatozoa are unlikely to occur and therefore, separation by this method is unlikely to be successful.

2.1.3 Discrimination by the Presence of F-body

It is said that when spermatozoa are stained with quinacrine, a fluorescent dye, the Y-chromosome is specifically stained as the F-body in such species as the gorilla and man, and thus X- and Y-bearing spermatozoa can be discriminated when stained with quinacrine. However, this may mot hold true for species other than the gorilla or man, because the ratio of spermatozoa having the F-body to those without the F-body is not 50:50. Therefore the Y-chromosome-specific staining technique is theoretically unlikely, i.e., this method seems unlikely to yield accurate results, in principle.

2.1.4 Separation by Flow Cytometry

The X-chromosome is slightly larger than the Y-chromosome. After fluorescent staining of the X- and Y-chromosome, more intense light is emitted from the X-chromosome. This fluorescent staining difference is a basis for separating X-chromosome bearing spermatozoa from Y-chromosome bearing spermatozoa. Insemination of eggs with spermatozoa thus separated enables the production of male or female embryos as desired.

This flow-cytometric method has drawbacks, however, such as the need for the laborious pretreatment of spermatozoas. For example, pretreatment may include dye-staining the spermatozoas and irradiation of the spermatozoa with a laser beam. The spermatozoa may be damaged in such treatments. Micro-insemination, which relies on expensive instrumentation, is necessary for transferring desired spermatozoa identified by flow cytometry. Because of the drawbacks and difficulties of this method, it has not been used commercially yet.

2.1 Anti-HY Antigen Antibody (HY Antibody) Method

A skin graft transplanted from a male to a female in an animal inbred strain is rejected and drops off. The inverse graft from a female to a male is accepted. This phenomenon is considered to be caused by a histocompatibility antigen called the HY antigen which is mapped on the Y-chromosome. The graft rejection reaction is under the control of the cellular immunity. However, anti-HY antibody was also found in the blood of a female rejecting a male graft, indicating the involvement of the humoral immunity.

The HY antigen is expressed at early developmental stages; it has been said to be expressed at the 8 cell stage in mice. There are reports that sexing of murine embryos was possible using the HY antibody derived from mice. It was also claimed that morphological changes of bovine embryos treated with the HY antibody from rats enabled discrimination of male embryos from female ones.

Since the immunogenicity of the HY antigen is considered to be common among species, the HY antibody derived from rats and mice can be applied to cattle. A convenient aspect of using the HY antibody for sexing purposes is that it is not necessary to sample a part of an embryo to determine sexing results.

However, because the HY antigen is not a major histocompatibility antigen but a minor one, its immunogenicity is weak. It is difficult, even impossible, to induce the antibody in some strains. Sometimes the titer of the HY antibody is too low for detection. Determination of the anti-HY antigen/antibody reaction for sexing is not always clear-cut. These drawbacks prevent this method from becoming a reliable sexing method.

2.3 Cytogenetic Method

2.3.1 Method Utilizing the Sex Chromatin

Through inactivation of one X-chromosome of the two X chromosomes in mammalian females, the X-chromosome gene dosage between males and females is equalized. The inactivated X-chromosome is seen in the nucleus as a sex-chromatin. Since the inactivation occurs early in the development, the presence or absence of the sex-chromatin in a part of the trophectoderm microsurgically isolated from a blastocyst would allow prediction of the sex of the embryo. This method is partly successful in mice and rabbits, but cytoplasmic particles obstruct the observation of the sex-chromatin in other domestic animals. This method is not practically used.

2.3.2 Identification of Sex Chromosomes

Direct identification of X,X-chromosomes or X,Y-chromosomes provides a reliable sexing method. The direct identification technique involves bisecting an embryo, with one half being used for embryo transfer and the other, for cytogenetic analysis. Fortunately, all 58 autosomes of cattle are V-shaped telocentric. The X-chromosome of cattle is large and submetacentric, whereas the Y-chromosome of cattle is small and submetacentric. When cattle sample specimens are good, identification of sex chromosomes is easy. When poor metaphase spreads are obtained, the sexing ratios are reduced. Good metaphase spreads are not always obtainable, however, which limits the practical utility of this method.

3. SUMMARY OF THE INVENTION

The present invention provides PCR primers with which sexing of bovine embryos can be easily attained and provides a practical, rapid and reliable method for determining the sex of bovine embryos using these primers. The invention provides isolated DNA sequences which hybridize specifically to bovine male genomic DNA as well as other isolated DNA sequences which hybridize specifically to both male and female bovine genomic DNA.

Sexing methods of bovine embryos are characterized by discriminating PCR products, which are obtained by amplifying specific DNA sequences in a PCR reaction with two pairs of male-specific and gender-neutral primers. These primers were derived from DNAs which specifically hybridize to the bovine male genome and from DNAs which gender-neutrally hybridize to both bovine male and female genomes.

BRIEF DESCRIPTION OF DRAWINGS

FIGS. 1a, 1b, 1c, 1d and 1e. Schematic illustration of cloning method for male-specific DNA fragments. FIG. 1a illustrates bovine female DNA fragments with non-specific end sequences; FIG. 1b illustrates bovine male DNA treated with a type II restriction enzyme; FIG. 1c illustrates the mixing of bovine male fragments having specific type II restriction enzyme ends and bovine female fragments with non-specific end sequences; FIG. 1d illustrates a cloning vector that has specific type II restriction enzyme ends; FIG. 1e illustrates the selective cloning of bovine male DNAs having type II restriction enzyme ends into the vector having specific type II ends.

FIG. 11a illustrates a male demi-embryo having the X- and Y-chromosomes. FIG. 11b illustrates a female demi-embryo having two X-chromosomes. In FIG. 11a and 11b, long arrows indicate the X-chromosomes and the short arrow indicates the Y-chromosome.

5. DETAILED DESCRIPTION

Figure 2:
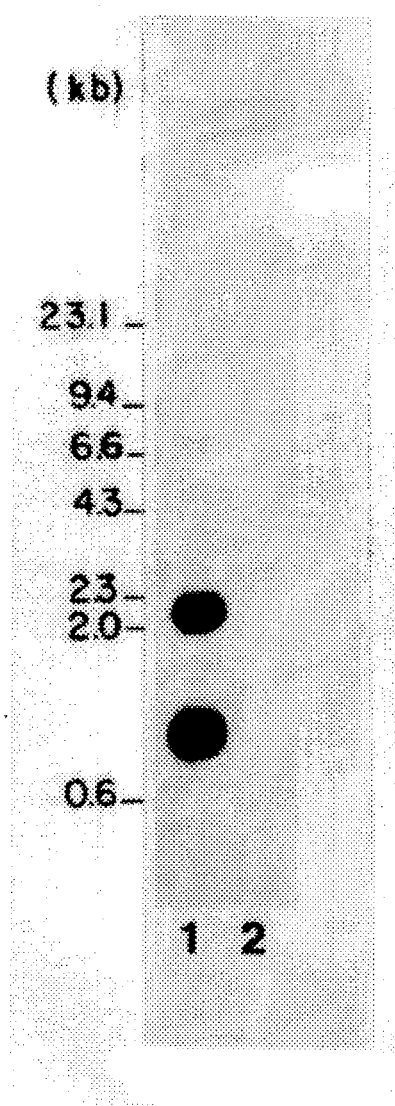
FIG. 2. Electrophoresis of a clone which specifically hybridizes to male bovine DNA.

5.1 Basis for the Selection of PCR Primers of the Present Invention

As the DNA polymerase chain reaction (PCR) (Science, 239, pp487–491, 1988) is now well established, attention has been paid to development of a simple and reliable sexing method using Y-chromosome specific DNA probes, which could overcome the drawbacks of previous methods as described in Section 2.

Since a part of a template DNA can be amplified millions of times, sexing of embryos would be possible if Y-chromosome specific sequences could be demonstrated by PCR in a small sample from the embryos.

The problems faced in developing an accurate and reliable PCR technique for sexing of embryos are obtaining appropriate Y-chromosome-specific sequences, identifying primers to use for PCR amplification, and developing the actual PCR procedure.

Sequences used in the present invention should meet the following conditions.

5.1.1 Disadvantageous PCR Primer Sequences

A. Sequences on the Pseudoautosomal Region Are Not Used

Sequences found on the pseudoautosomal regions are not used to provide PCR primers for the purpose of sexing embryos. Crossing-over occurs between the X-and Y-chromosome at meiosis. The pseudoautosomal region in which genes such as MIC2 are located (P. J. Goodfellow et al., Science, 234, 741–743, 1986) shows 99% homology between the X- and Y-chromosome. Accordingly, discrimination of male and female embryos using PCR primers from the pseudoautosomal region is difficult. Therefore, primers from this region are not suitable for the present invention.

B. Not all the Y-Chromosome Specific DNAs Are Effective

Not all the Y-chromosome specific DNAs are effective for providing PCR primers for the purpose of sexing embryos.

The Zfy gene (D. C. Page et al., Cell, 51, 1091–1104, 1987), for example, is a unique sequence on the Y-chromosome. However, there is a similar sequence on the X-chromosome. Genes like the Zfy gens, i.e., genes unique to one sex, but similar to genes of the opposite sex, are difficult to use for sexing embryos, because there is the possibility that almost the same length of DNAs will be amplified from both male and female embryos.

C. A Unique Sequence, Even If It Is Y-Chromosome-Specific, Is Disadvantageous Even Y-chromosome specific genes may be disadvantageous for providing PCR primers for use in sexing embryos. The Sty gens (A. H. Sinclair et al., Nature, 346, 240–244, 1990), for example, is uniquely located on the Y-chromosome and there are no similar genes on the X-chromosome and autosomes. This fact eliminates the problem discussed in section 5.1.1 B. In using Y-chromosome specific genes, even Y-chromosome specific genes having similarity to X-chromosome genes as discussed in section 5.1.1 B, a further obstacle is encountered. A single sequence of 200–300 bases has to be amplified from approximately 3,000,000,000 bases of a genome. This type of PCR amplification reaction, i.e., amplifying a few hundred bases found in a total of approximately 3 billion bases, is not efficient. A tiny contaminant in the PCR reaction may lead to failure. These unique sequences therefore are disadvantageous for sexing embryos by means of a PCR technique.

5.1.2 Advantageous PCR Primer Sequences

A. Y-Chromosome-Specific, Repeated Sequences Are Suitable

Y-chromosome specific, repeated sequences are the preferred source of DNA for use as PCR primers of the present invention. If sequences repeated hundreds or thousands of times or more on the Y-chromosome are available, these would be most suitable due to the principle of the PCR.

B. A Gender-Neutral Primer Is also Needed As An Internal Control

Gender-neutral primers are also needed in the method of the present invention to serve as internal controls. Repeated gender-neutral DNA sequences are desirable as internal controls.

Embryos from which Y-chromosome-specific DNAs are detected through PCR amplification using Y-chromosome specific repeated sequences as PCR primers are males and the others are females, theoretically. However, since the PCR reaction is supersensitive, i.e., minute contamination by undesirable DNAs or a slight deviation of the experimental conditions may affect amplification signals, the possibility exists that male samples will not show male signals, or that female samples will give male signals. To verify experimental results, PCR primers giving a gender-neutral signal are needed as internal controls to the PCR reaction. The object of the method of the present invention, i.e., the method for sexing bovine embryos, is for male samples to give both male-specific and gender-neutral signals upon PCR amplification, while female ones should give only a gender-neutral signal upon PCR amplification.

5.2 PCR Primers of the Present Invention

PCR primers meeting all the requirements described in Section 5.1 were obtained and are listed in the Sequence Listing, and listed in the Example. By using these primers, a reliable and rapid method for sexing bovine embryos is provided by the present invention.

The present invention provides a method of sexing bovine embryos characterized by DNA primers that specifically hybridize to bovine male genome, DNA primers that gender-neutrally hybridize to both male and female genomes, template DNAs derived from isolation of a small amount of cellular sample from blastocysts, amplification of specific DNA sequences by conducting a PCR reaction, and identification of the PCR products for sexing purposes.

5.3 Preparation of DNA Probes of the Present Invention

5.3.1 Isolation of Bovine Male-Specific DNA Clones

Bovine female DNA is isolated by the method of phenol extraction (J. Sambrook et al., Molecular Cloning, A. Laboratory Manual, 2nd ed., Cold Spring Harbor Laboratory Press, 1989). DNA fragments of preferably length around 1000 bases without specific end sequences are prepared by techniques known in the art, for example, the ultrasonic treatment of isolated female DNA.

In addition, DNA fragments with specific ends are prepared by digesting bovine male DNA isolated by the method of phenol extraction (J. Sambrook et al., supra) with a restriction enzyme of type II, for example Mbo I, which cuts DNA at ↓ GACT sites. The male and female DNA fragments thus prepared are mixed, denatured to single-stranded DNAs and subjected to the reassociation reaction. The mixing ratio of the two DNAs is selected to give an excess of female DNA, e.g., 20 to 1000-fold. A desirable ratio is 50:1. To denature double stranded DNAs to single-stranded DNA, various methods, e.g. heat treatment and alkaline treatment, can be used. The reassociation reaction can be done by any established method. The method employing phenol, which accelerates the reassociation, is favorable.

Since X-chromosomal and autosomal male DNAs are common to female DNAs, upon reassociation of DNA strands, most male DNAs hybridize to complementary female DNAs which exist in excess. Because these hybrid molecules consist of female DNAs without specific ends and male DNAs with specific ends produced by digestion with a restriction enzyme of type II, the ends of the hybrid DNAs do not match.

The Y-chromosome-specific male DNAs, however, cannot find complementary strands of female DNAs and therefore hybridize to their partners, i.e., their own complementary strands, to form the original double stranded Y-chromosome-specific male DNAs with ends having a specific type II restriction enzyme recognition site.

When double-stranded DNAs thus obtained are ligated into a cloning vector having specific type II restriction enzyme ends, the male-specific DNAs are selectively cloned into the vector DNAs. This cloning process is shown in FIG. 1. An example of a cloning vector useful in the present invention is pUC118 (Takara).

The recombinant cloning vectors described above are transfected into a host and those clones containing bovine DNAs are selected by using appropriate markers. Clones containing the desired DNAs are isolated.

Markers useful in the present invention depend on the vectors used and include resistance to antibiotics such as ampicillin and tetracyclins, and hydrolytic activity towards X-gal, a dye. Isolation of clones with expected DNAs can be done either by Southern blot hybridization, where plasmid DNA extracted from each colony is radioactively labelled by methods known in the art and is hybridized to bovine male DNA, or by the plaque hybridization method when the cloning vectors are phages. Sequences of thus cloned DNAs can be determined by methods of DNA sequencing known in the art, e.g. Sanger's method.

For isolation of different clones specific to bovine males, screening of bovine male DNA libraries with male-specific DNA fragments as described in this section is conducted. DNA sequences of these secondary clones can also be determined by DNA sequencing methods well-known method in the art, e.g. Sanger's method.

5.3.2 Isolation of DNA Clones Which Gives Differential Southern Blot Images between Bovine Males and Females By screening bovine genome libraries with DNA probes obtained as described in section 5.3.1, many clones can be isolated.

Most of these clones contain bovine Y-chromosome DNAs of 15–20 kb. These long sequences sometimes contain DNAs hybridizable to the X-chromosome and/or autosomes in addition to Y-chromosome-specific DNAs.

When DNAs are isolated from these clones, purified, and then used as probes for Southern blot hybridization, differences in electrophoretic patterns such as the number of bands and the intensity in the autoradiogram are observed between males and females.

There are two ways to obtain PCR primers for sexing from these clones. Firstly, DNAs are digested to smaller fragments by using restriction enzymes or by some other method known in the art, and then fragments which hybridize specifically to males and gender-neutral fragments are subcloned. Secondly, after determining all the sequences of the subcloned fragments, PCR primers are randomly synthesized from these fragments and PCR products are examined to see if they are male-specific or gender-neutral.

5.3.3 Isolation of DNA Fragments Which Hybridize to Both Male and Female DNAs As shown in section 5.3.2, gender-neutral fragments can be extracted from DNAs which show differential Southern blot images between males and females, either by subfractionation or examination of primers which give gender-neutral PCR products. On the other hand, the Y-chromosome contains many DNA fragments which hybridize to both the X-chromosome and autosomes. Therefore, it is probable that gender-neutral fragments are isolated during the process of cloning male-specific DNAs as described in 5.3.1. Since the sequences of these DNAs, once cloned, can be determined by DNA sequencing methods known in the art, these clones are useful to make gender-neutral primers.

5.3.4 Preparation of PCR Primers

DNA sequences and their complementary sequences i.e., complementary strands, which hybridize male-specifically or gender-neutrally obtained as described in 5.3.1, 5.3.2, and/or 5.3.3, can be used to prepare PCR primers. The length of primers is usually around 10–40mer with a practically convenient length being 15–25mer. Primers can be prepared by digesting DNAs obtained as described in sections 5.3.1, 5.3.2, and/or 5.3.3 with restriction enzymes, denaturing the restriction digested fragments, and purifying the resultant single-stranded DNAs. Primers can be synthesized by methods known in the art, for example with a DNA synthesizer. Simplicity and reliability of preparation make the method of DNA synthesis preferable.

5.4 The Method of Sexing Bovine Embryos

Target embryos for sexing should be developed sufficiently that a sampling of embryonic cells does not cause critical damage to them. Target embryos for sexing should not be over-developed, because it is desirable that embryos cultured in vitro show no degeneration. From this point of view, use of blastocysts, in which the trophectoderm and inner cell mass have been developed, is desirable.

Figure 8:
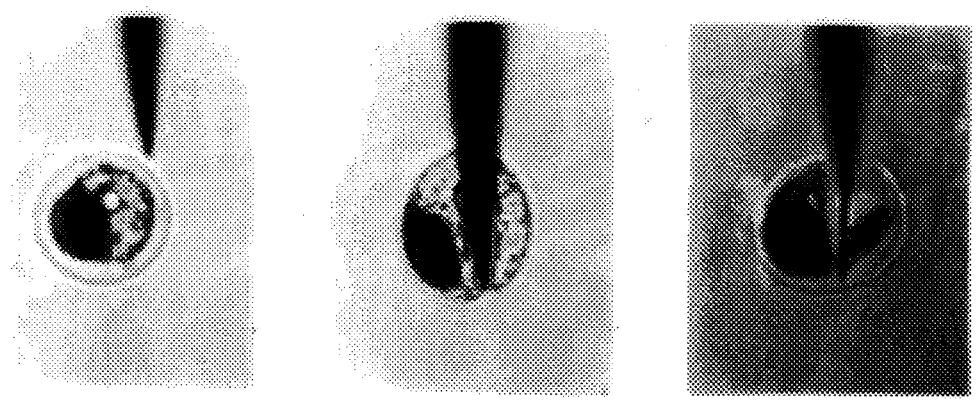
FIG. 8. Method to cut out a part of the trophectoderm after allowing a blastocyst to attach to the surface of a culture dish.

Sampling of cells from blastocysts is performed by methods known in the art, and is shown in FIG. 8. First embryos are transferred from culture medium into an appropriate physiological fluid such as Dulbecco's modified phosphate-buffered saline.

Sampling should be done after blastocysts have become attached to the surface of the dish firmly because of reliability. Micro-blades can be used for sampling. Parts of embryos to be sampled should be selected so that damage to embryos is as small as possible, e.g. a part of the trophectoderm. Ten cells are sufficient for sampling.

DNAs can be extracted from these cells by methods known in the art and are used as templates for the PCR reaction. Two pairs of primers are used in the PCR reaction for embryo sexing, one pair being male-specific, with the second pair being gender-neutral.

After the PCR reaction is allowed to proceed, the PCR products are analyzed by gel electrophoresis and stained with a fluorescent dye. Male embryos give two bands, one male-specific with the second being gender-neutral, while female embryos give a single gender-neutral band, thus enabling reliable sexing of embryos.

Primers for the PCR reaction described above have to be selected carefully to meet two criteria. The lengths of PCR products need to be sufficiently different to allow clear differentiation between the male-specific sequence and the gender-neutral one. Secondly, the lengths of the anticipated PCR amplification products should not be longer than a length compatible with the activity of DNA polymerase. The difference of the lengths of PCR products should be at least 20 bases and preferably, around 50–100 bases. The length of each PCR amplification product should be restricted to 100–500 bases and preferably restricted to 150–300 bases.

5.5 Conclusion

The present invention provides PCR primers for simple sexing of bovine embryos and a reliable and rapid method for the sexing by the PCR technique. The present invention is explained concretely by means of Examples.

6. Example: Isolation of a Clone Having DNA Which Hybridizes Specifically to Bovine Male DNA

6.1 Materials and Methods

DNA was prepared from the liver of a bovine female (Holstein) by the method of phenol extraction (J. Sambrook et al., Molecular Cloning, A laboratory Manual, 2nd ed., Cold Spring Harbor Laboratory Press, 1989). The DNA (200 µg) was sonicated to give fragments of around 1000 base pairs.

Bovine male DNA (Holstein) Was also prepared as described above and 20 µg of it was digested completely with 100 units of a type II restriction enzyme. MboI (Takara Shuzo Co., Ltd), which cuts DNA at ↓ GACT sites.

Female DNA fragments (50 μg) and male ones (1 μg) thus prepared were dissolved in 250 μl of distilled water and heated to 100° C. to denature the double-stranded DNAs into single-stranded DNAs. The solution was made up to 1 ml by adding 1M phosphate buffer (pH 6.8, 120 μl), 5M NaCl$_4$ (250 μl), phenol (81 μl), and distilled water (299 μl) and was shaken for 93 h at room temperature. After phenol extraction, DNA was precipitated from the aqueous phase with ethanol and dissolved in 20 μl of Tris-EDTA buffer. An aliquot (1 μl) was mixed with 200 μg of a plasmid vector pUC118 (Takara), which had been digested with a restriction enzyme BamH1 (cutting site: G↓GATCC, Takara) and of which the 5'-phosphate residues had been removed. The mixture was treated with a ligation kit (Takara) at 16° C. for 2 h to obtain recombinant plasmids with insert DNAs having GACT ends.

The reaction mixture described above was used directly to transfect E. coli DH 5α (obtained from the Institute of Applied Microbiology, The University of Tokyo) by a well-known method. The transfectants were plated on LB agar plates containing X-gal (40 μg/ml), IPTG (40 μg/ml), and ampicillin (50 μg/ml). After incubation, 400 white colonies, i.e., recombinants lacking the ability to hydrolyze X-gal, were isolated, DNA was extracted from each colony by a well-known method and was examined to see if it was derived from the bovine Y-chromosome DNA. For this, each plasmid DNA was labelled with $^{32}$P by the random primer method and was hybridized to male and female DNAs, 10 μg of each of which had been completely digested with 100 units of EcoRI (Takara) at 37° C., gel-electrophoresed, and transferred to a nylon membrane. The presence of bovine male-specific DNA in each plasmid was examined by making an autoradiogram.

6.2 Results of the PCR Reaction: Identification of SEQ ID NO:1, 8SEQ ID NO:2 and SEQ ID NO:3

The result showed that a plasmid DNA specifically hybridized to bovine male DNA (FIG. 2, lane 1. Lane 2 shows the result with bovine female DNA). The sequence of this DNA determined by Sanger's method is shown in SEQ ID NO:1. The plasmid having this DNA sequence was transfected into E. coli by methods well-known in the art and the transfectant, E.c. 118-bms1, has been deposited as FERM BP-4095 in the Fermentation Research Institute, The Agency of Industrial Science and Technology, the Ministry of International Trade and Industry.

For security, other clones were sought. The SEQ ID NO:1 mentioned above was used as a probe to screen a bovine malegenomic library made by methods known in the art, i.e., by recombining the EMBL3 phage vector (Stratagene) with partially MboI-digested male bovine genomic DNA. The plague hybridization of a SEQ ID NO:1 probe hybridized to 250,000 clones (out of a total library of 500,000 clones) yielded 28 positive clones hybridizing to the probe. One of them was picked up and its DNA was extracted. The DNA was completely digested with EcoRI at 37° C. Each EcoRI fragment was examined by Southern hybridization for male specificity. The sequences of DNA fragments thus obtained were determined by Sanger's method to be as shown in SEQ ID NO:2 and SEQ ID NO:3.

Figure 3:
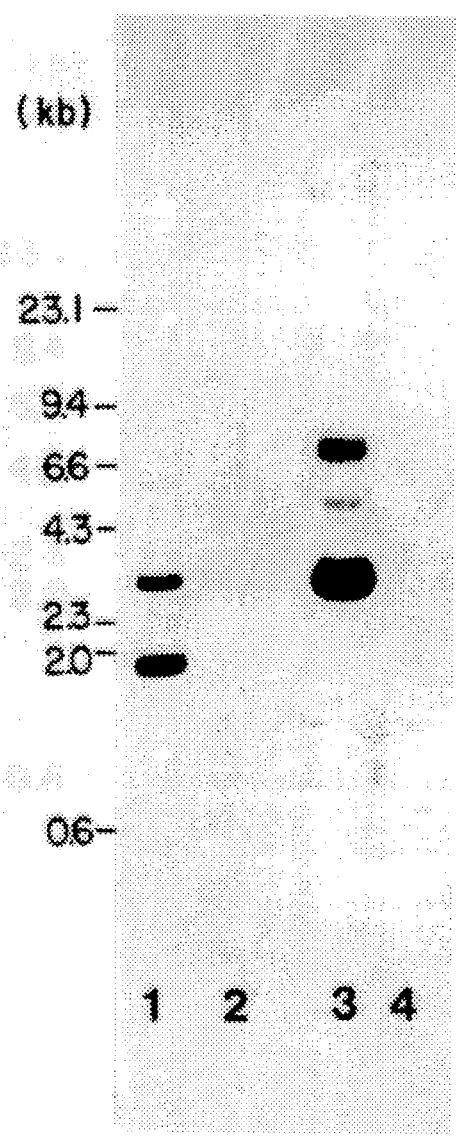
FIG. 3. Electrophoresis of secondary clones which specifically hybridize to male bovine DNA.

The results of the Southern blot analyses using DNA sequences shown in SEQ ID NO:2 and SEQ ID NO:3 are presented in FIG. 3, where lanes 1 and 2 are the results with SEQ ID NO:2 and lanes 3 and 4, with SEQ ID NO:3. Lanes 1 and 3 show hybridization patterns with male DNA and lanes 2 and 4 show hybridization patterns with female DNA.

These results demonstrated that both DNA's shown in SEQ ID NO:2 and SEQ ID NO:3 specifically hybridize to the male DNA.

DNAs shown in SEQ ID NO:2 and SEQ ID NO:3 were introduced into E. coli by a well-known method and the resultant recombinants E.c.gem-bms1 and E.c.gem-bms2 have been deposited as FERM BP-4089 and FERM BP-4090 respectively, in the Fermentation Research Institute, The Agency of Industrial Science and Technology, the Ministry of International Trade and Industry.

6.3 Conclusions

The original phage, containing DNA SEQ ID NO:1, was one of 28 clones selected from 250,000 plaques, indicating approximately one positive clone per 10,000 plaques. The intensity of the Southern blot images suggests that each clone may contain 10–100 copies. Theoretically, in order to screen out a gene which exists only once in the human genome usually requires screening 1,000,000 plaques. Roughly speaking, the copy number of the original phage clone may be 1,000–10,000 of the total genome. Accordingly, secondary clones can be quite easily isolated if one uses DNAs shown in SEQ ID NO:1, SEQ ID NO:2, or SEQ ID NO:3 as probes. PCR products are amplified approximately twice per PCR reaction cycle. One thousand is nearly $2^{10}$ and 10,000 is $2^{13}$. Theoretically, therefore the number of PCR reaction cycles for this multi-copy DNA can be reduced by 10–13 times as compared with amplification of a single copy gene.

7. Example: Isolation of a DNA Clone Which Gives Differential Southern Blot Images Between Bovine Male and Female DNA, Identified As SEQ ID NO:4

Figure 4:
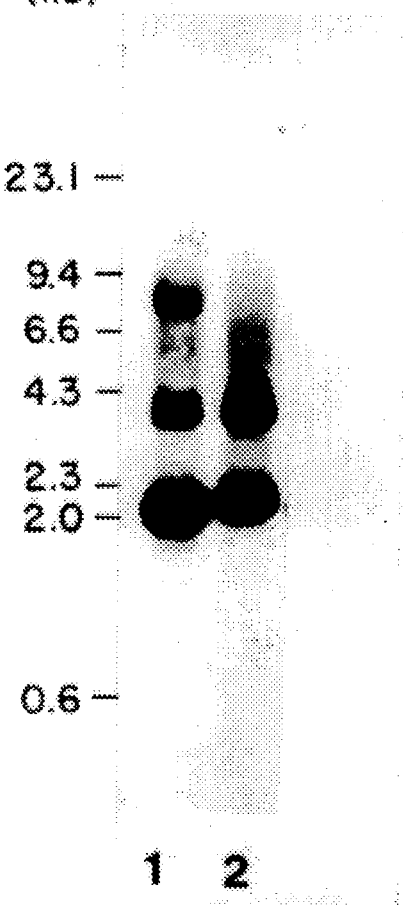
FIG. 4. The Southern blot images (as shown by electrophoresis) of DNAs of the present invention wherein one DNA specifically hybridizes to male DNA and the other, gender-neutrally to both male and female DNA.

One clone was selected from the 28 clones described in Example 6 and its DNA was extracted. One of the EcoRI fragments was isolated and sequenced. The result is shown in SEQ ID NO:4. This EcoRI fragment, consisting of 2104 base pairs, was labelled with $^{32}$P and was used as a probe for Southern blot analysis. The result is shown in FIG. 4, where lane 1 is the hybridization pattern with male DNA and lane 2, that with female DNA. DNA of SEQ ID NO:4 hybridized to both male and female DNA, but images were different from each other.

DNA having SEQ ID NO:4 was introduced into E. coli by a well-known method and the recombinant E.c.gem-bms3 has been deposited as FERM BP-4091 in the Fermentation Research Institute, The Agency of Industrial Science and Technology, the Ministry of International Trade and Industry.

8. Example: Isolation of DNA clones Which Hybridize to Both Bovine Male and Female DNA Gender-Neutrally, Identified As SEQ ID NO:5, SEQ ID NO:6, and SEQ ID NO:7

When male-specific clones were explored as described in Example 6, 20 clones were found to hybridize to both male and female DNA in the Southern blot analysis. These were utilized for the present purpose. Taking into consideration the intensity of hybridization images, three clones which were expected to be repetitious were selected. As was done above in Example 6 and 7, sequences of EcoRI-HindIII fragments of these clone DNAs were determined and are shown in SEQ ID NO:5, SEQ ID NO:6 and SEQ ID NO:7. These EcoRI-HindIII fragments were labelled with $^{32}$P and used as probes for the Southern blot analyses. The results are shown in FIG. 5.

Figure 5:
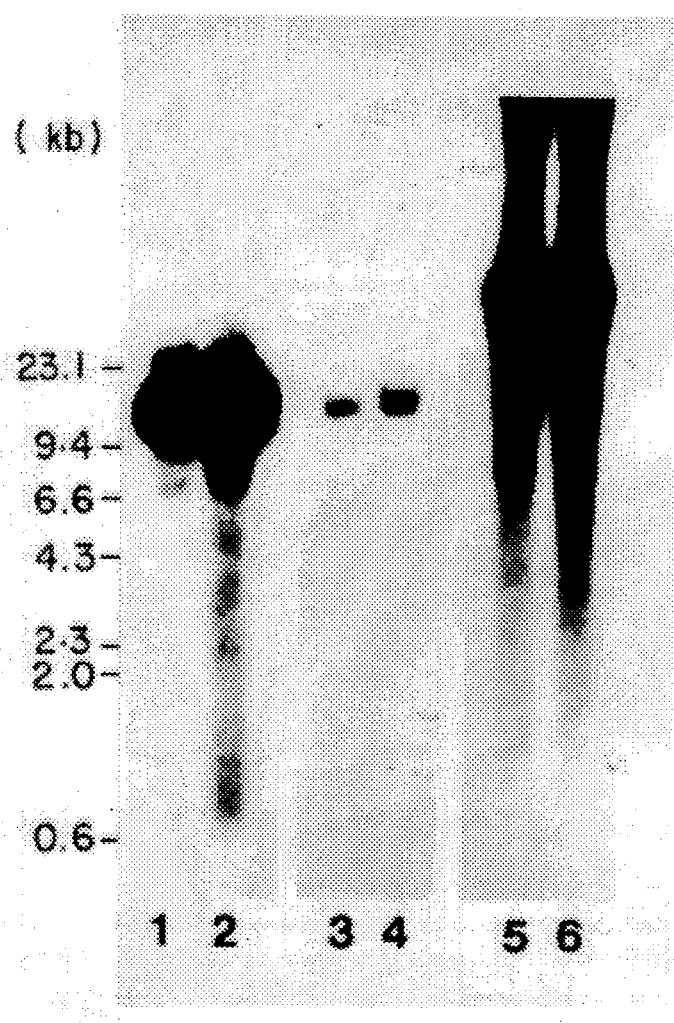
FIG. 5. The Southern blot images (as shown by electrophoresis) of clones which gender-neutrally hybridize to DNA.

In FIG. 5, lanes 1 and 2, lanes 3 and 4, and lanes 5 and 6 show the results of the Southern blot analyses with $^{32}$P-labelled probes of SEQ ID NO:5, SEQ ID NO:6 and SEQ ID NO:7, respectively. EcoRI-digested male DNAs were applied to lanes 1, 3, and 5 and EcoRI-digested female DNAs, to lanes 2, 4 and 6. These results indicate that the copy number of DNAs shown in SEQ ID NO:5 and SEQ ID NO:7 is quite large. DNAs consisting of SEQ ID NO:5, SEQ ID NO:6 and SEQ ID NO:7 were introduced into E. coli and the resultant recombinants, E.c.118-bmf1, E.c.118-bmf2, and E.c.118-bmf3, have been deposited as FERM BP-4092, FERM BP-4093 and FERM BP-4094 respectively, in the Fermentation Research Institute, The Agency of Industrial Science and Technology, the Ministry of International Trade and Industry.

9. Example: Synthesis of Primers for the PCR Reaction 9.1 Male Specific Primers

PCR Primers which gave male-specific bands were synthesized with a DNA synthesizer (ABI) on the basis of SEQ ID NO:1, SEQ ID NO:2, SEQ ID NO:3 and SEQ ID NO:4. Sequences of these primers are shown in SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:18 and SEQ ID NO:19.

Among these, combinations of primer SEQ ID NO:9 and SEQ ID NO:13, SEQ ID NO:8 and SEQ ID NO:13, SEQ ID NO:8 and SEQ ID NO:9, SEQ ID NO:14 and SEQ ID NO:15, SEQ ID NO:16 AND SEQ ID NO:17 and SEQ ID NO:18 and SEQ ID NO:19 gave male-specific PCR products. With the combination of SEQ ID NO:12 and SEQ ID NO:13, however, the PCR did not proceed.

9.2 Gender-Neutral Primers

PCR primers which gave gender-neutral bands were synthesized as described above on the basis of SEQ ID NO:5, SEQ ID NO:6, and SEQ ID NO:7.

Sequences of these primers are shown in SEQ ID NO:10, SEQ ID NO:11, SEQ ID NO:20, SEQ ID NO:21, SEQ ID NO:23, SEQ ID NO:24, SEQ ID NO:25, SEQ ID NO:26, and SEQ ID NO:27.

Among these, combinations of primer SEQ ID NO:10 and SEQ ID NO:11, SEQ ID NO:20 and SEQ ID NO:21, SEQ ID NO:22 and SEQ ID NO:23, SEQ ID NO:24 and SEQ ID NO:25 and SEQ ID NO:26 and SEQ ID NO:27 gave gender-neutral PCR products.

10. Example: Sex Discrimination with Bovine Male and Female DNA

Figure 6:
FIG. 6. Sensitivity of discrimination of sexes by the present invention with purified male and female DNAs (as shown by electrophoresis).

DNAs were amplified by 50 cycles of PCR with varied amounts of purified bovine male and female DNAs and primers of SEQ ID NO:8, SEQ ID NO:9, SEQ ID NO:10 and SEQ ID NO:11 (20 pmol each). The products were electrophoresed in agarose gel, stained with ethidium bromide, and photographed under UV irradiation (FIG. 6). In FIG. 6, lanes a, c, e, g, and i represent male DNA and lanes b, d, f, h, and j, female DNA. DNA (1 ng) was applied to lanes a and b, 100 pg to lanes c and d, 10 pg to lanes e and f, 1 pg to lanes g and h, and 100 fg to lanes i and j. Distilled water, the negative control, was applied to lane k.

The results indicate that 10 pg of DNA is enough to discriminate males from females (FIG. 6, e). Since the DNA content in one cell is approximately 3 pg, sampling of three cells from a blastocyst should be suffice for sexing.

11. Example: Sex Discrimination with Cultured Bovine Cells

Figure 7:
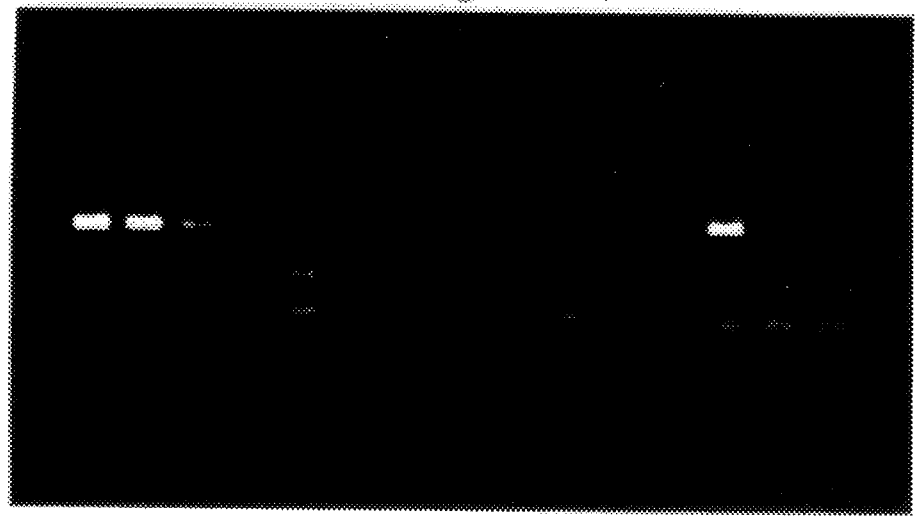
FIG. 7. Sensitivity of discrimination of sexes by the present invention with cultured bovine cells (as shown by electrophoresis).

Bovine fibroblast-like cell cultures were obtained from the liver of a male and female by a well-known method (The Japanese Tissue Culture Association (Ed.), Techniques for Tissue Cultures, 2nd Ed., Asakura Publishing Co., Tokyo, 1988, in Japanese). Cells were frozen in Tris buffer and then thawed for 30 min at 90° C. The cell suspension was serially diluted and subjected to the PCR reaction for sexing with primers of SEQ ID NO:8 and SEQ ID NO:9 under the same conditions as described in the above Example 10. In FIG. 7, PCR products from male cells were applied to lanes a–e and those from female cells, to lanes f–j. The expected numbers of cells used were 100 for lanes a and f, 30 for lanes b and g, 10 for lanes c and h, 3 for lanes d and i, and 1 for lanes e and j. PCR products from purified male DNA (10 pg) as used in Example 10 were applied to lane k and those from female DNA (10 pg), to lane 1. Lane k was PCR products of phosphate-buffered saline, the negative control.

The results show that 10 cells are enough for sexing.

12. Example: Sex Discrimination with Bovine Embryos

Blastocysts cultured in vitro by a well-known method were put in Dulbecco's modified phosphate-buffered saline (D. G. Whittingham, Nature 233, 125–126, 1971) and, by leaving them at room temperature for about 10 min. allowed to become attached to the surface of an untreated, plastic culture dish.

Figure 9:
FIG. 9. Sexing of demi-embryos by the present invention (as shown by electrophoresis).

A part of the trophectoderm was removed from the blastocysts by cutting with a microblade as shown in FIG. 8. The sample and remaining blastocyst were sexed by the method of the present invention using a PCR reaction with PCR primers of SEQ ID NO:8, SEQ ID NO:9, SEQ ID NO:10, and SEQ ID NO:11. This sexing method was the same as in Example 11. The results of this sexing are shown in FIG. 9, where lanes a and b represent results of the asymmetrically bisected samples from a single embryo, as do lanes d and e. The medium used to culture the embryos sexed here was used as the negative control and the PCR products were applied to lanes c and f. Lanes g and h are the positive controls, i.e., purified male and female DNA (10 pg each), respectively, as used in Example 11. As a result, both lanes a and b which were derived from the same embryo gave PCR products with the same lengths as the positive male DNA, implying that the original embryo was male. By the same token, the embryo used for lanes c and d was female, because PCR products were the same as the positive female DNA.

13. Example: Sex Discrimination with Bovine Embryos

Figure 10:
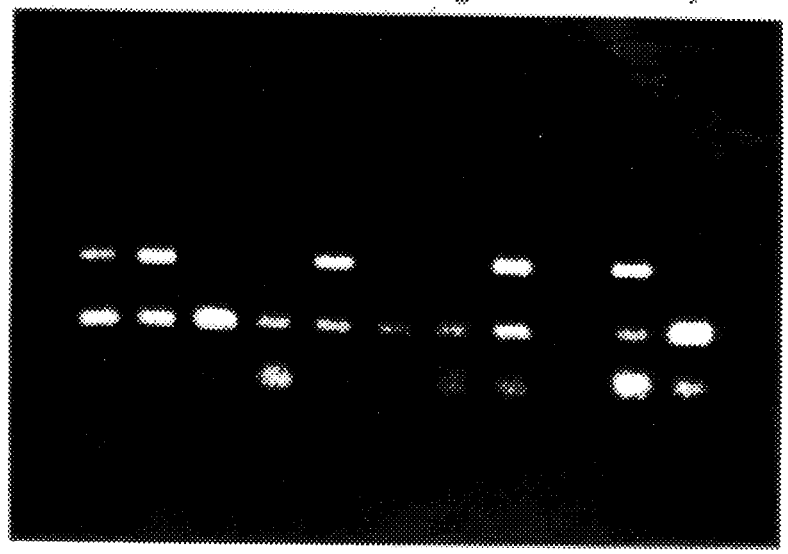
FIG. 10. Sexing of asymmetrically bisected embryos by the present invention (as shown by electrophoresis).
Figure 11A:
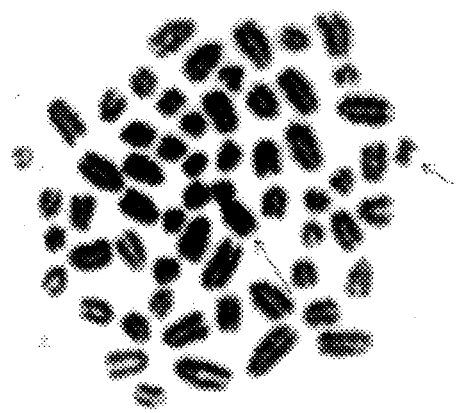
FIG. 11a and 11b. Microscopic images of karyotypes of demi-embryos.
Figure 11B:
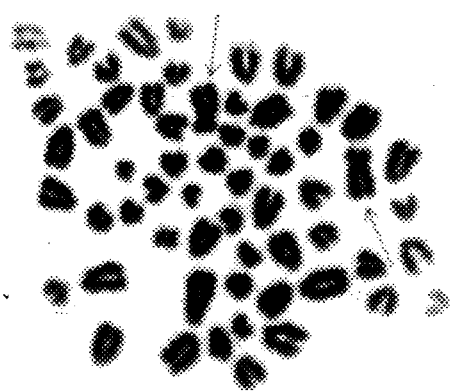

Blastocysts were bisected to obtain 8 pairs of demi-embryos and each demi-embryo was subjected to sexing by the same method as described in the Example 12. The results are shown in FIG. 10, where lanes a–h are results of the PCR with demi-embryos. Lane i represents the result with purified male DNA (10 pg) as used in Example 3 and lane j, the result with female DNA (10 pg). As a result, embryos in lanes a, b, e, f and h were Judged to be males and those in lanes c, d, and g, to be females. The other halves of the same embryos were cytogenetically examined under the microscope. Out of 8, karyotyping of samples corresponding to lanes c, e, and g were successful. The demi-embryo used for lane e was male, having the X- and Y-chromosome as shown in FIG. 11, a, and those used for lanes c and g were females, having two X-chromosomes as shown in FIG. 11, b. Demi-embryos for this karyotyping were cultured in TCM-199 medium (L. Leibfried and N. L. First. J. Anim. Sci., 53, 76–86, 1978) in the presence of Colcemid (0.04 μg/ml) for 2 hr at 37° C., treated with a hypotonic solution (0.9% sodium citrate) for a few minutes, fixed with a mixture of methanol: acetic acid:distilled water (3:2:1), applied to glass slides, stained with Giemsa's fluid, and then examined under the microscope. Long arrows indicate the X-chromosomes and the short arrow, the Y-chromosome in FIG. 11.

A number of references are mentioned throughout the specification, the disclosure of each of which is incorporated herein in its entirety by reference. In addition, priority benefits of Japanese Patent Application No. 352032/1991 filed Dec. 13, 1991 are claimed under 35 U.S.C. § 119 and the entire disclosure of this priority application is incorporated herein by reference.

We claim:

1. A method for sexing bovine embryos, comprising conducting a PCR reaction wherein a small part of a bovine embryo provides the DNA template for the PCR reaction and wherein a first and a second pair of isolated single stranded DNA molecules are used for the PCR; wherein said first pair of DNA molecules consists of 10–40 contiguous nucleotides from a DNA molecule selected from the group consisting of SEQ ID NO:1, SEQ ID NO:2, SEQ ID NO:3 and SEQ ID NO:4 and said second pair of DNA molecules consists of 10–40 contiguous nucleotides from a DNA molecule selected from the group consisting of SEQ ID NO:5, SEQ ID NO:6 and SEQ ID NO:7; subjecting the resultant amplified PCR products to gel electrophoresis; and analyzing the gel electrophoresis.

2. An isolated DNA molecule as shown in SEQ ID NO:4 which comprises two nucleic acid sequences, of which one nucleic acid sequence hybridizes specifically to bovine male genomic DNA and the other nucleic acid sequence hybridizes to both male and female bovine DNA.

3. A method of sexing bovine embryos according to claim 1 in which the first pair of isolated single stranded DNA molecules consists of isolated single-stranded DNA molecules which specifically hybridize to bovine male DNA wherein the DNA molecules consist of 10 to 40 contiguous nucleotides from a DNA molecule represented by the DNA sequence SEQ ID NO:2.

4. An isolated DNA molecule which hybridizes to both bovine male and female genomic DNA, wherein the isolated DNA molecule is represented by a DNA sequence selected from the group consisting of SEQ ID NO:5, SEQ ID NO:6, and SEQ ID NO:7 or a complementary strand thereof.

5. An isolated single stranded DNA molecule which specifically hybridizes to bovine male DNA, wherein the DNA molecule is represented by a DNA sequence selected from the group consisting of SEQ ID NO:8, SEQ ID NO:9, SEQ ID NO:12 and SEQ ID NO:13, or a complementary strand thereof.

6. A method of sexing bovine embryos according to claim 1 in which the first pair of isolated single stranded DNA molecules consists of isolated single stranded DNA molecules which specifically hybridize to bovine male DNA, wherein the DNA molecules consist of 10 to 40 contiguous nucleotides from a DNA molecule represented by the DNA sequence of SEQ ID NO:3.

7. A method of sexing bovine embryos according to claim 1 in which the first pair of isolated single stranded DNA molecules consists of the isolated single stranded DNA molecules which specifically hybridize to bovine male DNA, wherein the DNA molecules consist of 15 to 25 contiguous nucleotides from a DNA molecule represented by the DNA sequence of SEQ ID NO:3.

8. The DNA molecule according to claim 4 which is represented by the DNA sequence, SEQ ID NO:5.

9. The DNA molecule according to claim 4 which is represented by the DNA sequence, SEQ ID NO:6.

10. The DNA molecule according to claim 4 which is represented by the DNA sequence, SEQ ID NO:7.

11. A method of sexing bovine embryos according to claim 1 in which the second pair of isolated single stranded DNA molecules consists of isolated single-stranded DNA molecules capable of hybridizing to both bovine male and female genomic DNA, wherein the DNA molecules consist of 10–40 contiguous nucleotides from DNA molecules selected from the group consisting of SEQ ID NO:5, SEQ ID NO:6 and SEQ ID NO:7 or a complementary strand thereof.

12. A method of sexing bovine embryos according to claim 1 in which the second pair of isolated single stranded DNA molecules consists of isolated single-stranded DNA molecules capable of hybridizing to both bovine male and female genomic DNA, wherein the DNA molecules consist of 15–25 contiguous nucleotides from DNA molecules selected from the group consisting of SEQ ID NO:5, SEQ ID NO:6 and SEQ ID NO7 or a complementary strand thereof.

13. An isolated single stranded DNA molecule which hybridizes to both bovine male and female genomic DNA, wherein the DNA molecule is represented by a DNA sequence selected from the group consisting of SEQ ID NO:20, SEQ ID NO:21, SEQ ID NO:22 and SEQ ID NO:23, or a complementary strand thereof.

14. An isolated single stranded DNA molecule which hybridizes to both bovine male and female genomic DNA, wherein the DNA molecule is represented by a DNA sequence selected from the group consisting of SEQ ID NO:24, SEQ ID NO:25, SEQ ID NO:26 and SEQ ID NO:27, or a complementary strand thereof.

15. An isolated single stranded DNA molecule which hybridizes to both bovine male and female genomic DNA, wherein the DNA molecule is represented by a DNA sequence selected from the group consisting of SEQ ID NO:10 and SEQ ID NO:11.

16. A method for sexing bovine embryos, comprising conducting a PCR reaction wherein a small part of an embryo provides DNA templates for the PCR and first and a second pair of isolated single stranded DNA molecules are used for the PCR; wherein (i) said first pair of DNA molecules consists of DNA molecules selected from the group consisting of SEQ ID NO:8, SEQ ID NO:9, SEQ ID NO:12, SEQ ID NO:13, SEQ ID NO:14, SEQ ID NO:15, SEQ ID NO:16, SEQ ID NO:17, SEQ ID NO:13, SEQ ID NO:19, a combination of SEQ ID NO:9 and SEQ ID NO:13, a combination of SEQ ID NO:8 and SEQ ID NO:13, a combination of SEQ ID NO:8 and SEQ ID NO:9, a combination of SEQ ID NO:14 and SEQ ID NO:15, a combination of SEQ ID NO:16 and SEQ ID NO:17, and a combination of SEQ ID NO:18 and SEQ ID NO:19; and (ii) said second pair of DNA molecules consists of DNA molecules selected from the group consisting of SEQ ID NO:10, SE ID NO:11, SEQ ID NO:20, SEQ ID NO:21, SEQ ID NO:23, SEQ ID NO:24, SEQ ID NO:25, SEQ ID NO:26, SEQ ID NO:27, a combination of SEQ ID NO:10 and SEQ ID NO:11, a combination of SEQ ID NO:20 and SEQ ID NO:21, a combination of SEQ ID NO:22 and SEQ ID NO:23, a combination of SEQ ID NO:24 and SEQ ID NO:25, and a combination of SEQ ID NO:26 and SEQ ID NO:27; subjecting the resultant amplified PCR products to gel electrophoresis; and analyzing the gel electrophoresis.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 1404 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
GATCCTCTCA  CCTGTCCCAG  TCCCACAGGC  CTGGGCTGAT  GGGGTAGGCT  GGCGTGTGTT      60

CTCACCTGGG  GGCTGGATGA  GAACAGAGCT  ACTTTGAAAG  CGCCTCTGTA  CAATAAATGG     120

GCAGACTTCA  ATTCCTCTGG  CACTGGTGAG  TCATGGCTCT  TAGCGGGACA  CTGTTCTTAG     180

CATCTCCGGA  TTGAGAGATG  TTTCGTCTCT  AAATCTCTCT  CTACACAGAG  AAGTCCAGGT     240

TTGTGTCACA  TTTGGACACG  TGGGCAACAG  TCTTTTATGT  GAAGCGCGGA  ACTCGTTATT     300

TCCCGAAAGA  ATACATGCAT  TAAGTTTTCT  GCCAAGAAAT  GTGGCATTCT  CTCTGTTTCA     360

CCTGTGAAAA  TCTCACCACA  AACTTCCCAA  AAGGGAAATG  GAATTCTCTA  TATGTTATAT     420

GAATCATGGG  TGCACGTGTT  ATTTGCCGGC  ATGAAATTTG  GAATTCTGTG  TATTTCCCGT     480

ATGAAAACTT  GGGTGCTGAC  TTTTGCACAT  GAAATCTGGA  ATGTCGTGTA  TTAAACTTAG     540

GAACATCAGG  CCACTGATTT  TAGCACACAA  AATACGGAAT  TTTGATGACT  TTACGTATGT     600

AATCCGGGGC  ACTGATTTTT  CCTCTGTTGA  GTACAGATTT  CCTTACATGT  CTTTATCTTT     660

CCTCTGTAAG  AAAATCGTGG  CAGAGACTTA  GTCCATGAGC  TAATGAACTG  TTTATATTTC     720

ATGTAGGAGA  ATCTGGGTCG  TGATTTTCCT  ACATGAAACA  TGCAGTTCTC  TGTATTTAAT     780

GAATGAACAT  CCGGGCACCG  ATTTTCCTGC  CTTGAATATG  GGTTTCTCTA  CGTCGGCATT     840

TGAAACTCCA  GGCACGGAGC  TTTTCCCCGT  GAAATATGAA  ATTCTGGTAT  TTCACGTTGA     900

ATTGGGCATA  AACAAGGTAA  CACGAAATAC  GGAATTTTTC  ATCTTTCTCA  TTTGAAAATC     960

TGTGTGCTGA  CTTGCGTTAT  GAGTTACAGA  ACACTGTATA  TGTAACAACT  GAAAGAATTG    1020

GCCTCGATTT  TCCTACACAA  AATATGGAAT  TTTCTATTTC  ATACATAAAG  TGATTTTCAC    1080

ACTTGAGGTA  TGAAGTCACT  GTCAATGAAA  ACACGAAGTC  AATCCTTGTT  CAAGGTGATG    1140

AACAGGTAAG  TCAAAAACCT  TGAGCATGTG  ACCACACCTG  AAAGGGAACC  CTGAATGTTC    1200

TGAAACTCTG  AGACTGGATA  AAACCTGGTC  TTTTATGCAA  AATGGGGGGA  CAGAAGTACT    1260

AACTAAGAGC  CCTAACCCCA  AGACCTGGAT  GTTTCCTCTT  TAGCCACACT  CACTCTTGAG    1320

CAGGGTTGCT  TTAAAAAGCC  ACATGTAAGA  ACAATCAGTC  TGGGGACAGC  GGACAGCCGT    1380
```

```
GGTCAGCCGG CCTGGTGTGA ATTC                                                            1404
```

( 2 ) INFORMATION FOR SEQ ID NO:2:

( i ) SEQUENCE CHARACTERISTICS:
        ( A ) LENGTH: 1655 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
GAATTCGTGA GATGCAGATC TAGACGTGCT TATAATTTTA AATGCTTGTA TTAGAAAAGA    60
ATAAAAGCCT AAGCCAGTGG AAAGAGAAAT GGCAAACTCC GTCAAGGCTT TCAGCAAAGG   120
CCACATAGAG GAAACGTGAG GGAGGGGTGT GATTAGCCGG TGCAAACTTC TTGCTGTCAC   180
ATCTTGTGTT CTTGAGGTGA AGTGGTGGCC AGCTAACTGT GTCCTGCAAT CCTCAAGGGA   240
AACAAGTATG ATTCCCTATC CCCTGAAAGA GATTCCCCAG ATTGACTTTC ACCCTCCAAG   300
GTCCTGGTTG CGAGAAGGGG GTCCCCGTAT AGCCTGGTAG TCCCAGCTGG AAGAGGCAGG   360
TCTCAGTTCT CTGTGCCCTC CTCTTACCAA GGCCCCACA CACTGCCCGG CCACCTGCCA    420
TGAGGGAGCC AGGTACCCAG CACGCAGCTG ACCCTCAGCC TCCTCCGTCT ACCCAAATGG   480
GGAGCTCGGT CCTGTAGACT GTGGCCCATG ACATTGCCA CAACCATTCG ACATGGAGG     540
TGGGCATGGG ACACGGTGGC CGTTGCTTTG AAACCTGGGC CAGGCCGCTG AGTGGCTCCA   600
GCAAGGCCTC CGGGACTCTG CAAGACACAG CCTTTCCTCA CGCTTGTCCA AGCACCACAG   660
TTCATTACCC AGCCCAAGGC CCAAGGCTGG AAGGCCTGTG GGAAGGCTTT GATATCTCTC   720
TCAGTGCATT CAGCTGAGAG GCTTTCTGTT GGTGGTGTTG GGTTTGCGAA CTTCCCTAAT   780
GGTCTTGGCT GAGCTGCAGC TCCGTTTTCC ATCCTGCCTC TTTTACAGTG TCTTCCTGGA   840
TGAGCTGAGT CAACCTGTGA CTAAAAGATG GTAACGTGGA CCATCGGGGG CCATTTCCAC   900
TGGCCCGATG ACCACATCCT ACTCTCTTTC TATAACGCAG GGCTTTCAAC GTGACAATGT   960
CGTGTGATGT AAAAGCCTTC ATCTTCCTCG AACTCAAGTA TTTAACTCAG CATACTCTCC  1020
TCAAGAACAT GTATTGCATA CAGGGCTACC ATTTATTTTT TCACTGCCGG AATTATACTG  1080
GACATGTGAT GTACTTCCAA CCATTAATTT GGGGCCATAG TCACGTTACA GTGTTTCTTT  1140
GGTTTCTGCT GTGCGTGAAT CAAGTTTTAG CTGTACGTGT ATCCCGTCAA TTTTGGATTT  1200
CCTTCCCATT TAGGCCACCA CAGAGCAGTC GAGTCCCTTT CTTCTTTCAG TTTTTCTTTT  1260
TATTAAATTC AACTGGGGGT TAATTATGAT ACAATATTGT AATGGCTTCT GCCATGCATC  1320
AACATTAATA AGCCATAAGT ACACAGGGGT CCCAGCTATC CTGGAGCCGC TCCCACATCC  1380
CTGCCTACGC TATTCTTCGG GATTGCTCCA GAGCACTTGC TCTGCATTCC CTGATTCATG  1440
CAGATGAAAA CCAGAAAGAT GATTTTTCTG CATAAAATAT GCAATTGTCC TTCTTTCACA  1500
TGTGAGAACA TGGGTGCAGA GGTTTCTACC TGAAATAGGA AATCGGTATT TCATGTATGA  1560
AAATCGACTT GCATCATTTT CTTCATCATA TGTGGAATCT TGTGTCTCCC AGACGTATAT  1620
CTGTGCACAC GTTTTCCTAC ATGAGTGGGG AATTC                             1655
```

( 2 ) INFORMATION FOR SEQ ID NO:3:

( i ) SEQUENCE CHARACTERISTICS:
        ( A ) LENGTH: 3068 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
GAATTCCTCC  ACCTGCCAGG  ACAAAGTGTG  CGGGGTGGGG  TGGGTGTGAA  ACCTCTTTAC       60
AGAAGAGCTG  TCCTTTCCTG  TGTTAGGGAT  AGACCATGCC  CTCTCCCCTC  CCCAGTCACC      120
TCCCCTCCAC  AATCATCAGT  GTCCCCTGCC  TGACCTCCAA  GTTGGTCATG  AAGTGAAGCA      180
TGTCTGCATC  TTGCTTGCTC  ATCAAAACTG  ACATTTGGGG  GTGGTTCATA  AACTGCTTTA      240
GGTCAAGGAG  CCTCTAGATG  CTAGAGGTAA  AAGTGCTGGA  GAACAAAGC   TAGCCTAAAG      300
AGTAGAATGG  CCCTCCCTGT  TTGACTTCAA  CTTGCTACTG  GTTAACTCGT  CACATTTCGG      360
TTCACGCGGG  GCTATATGAA  TGCCGCACAA  GGTCCAAGCT  GTGCCCATGA  ATGCCCTACC      420
ACGAGGAGGT  TCTCTCCTAA  CCGGATAAGC  TTCATCTCAG  CCCCTTGAAA  GTTAGCTTAC      480
TTCGGGAAAA  CAAGCACTCC  TAGCTAGAAC  CCGTAGACCA  CTTACACTTC  CCCACCCCTC      540
CCCCATTCCA  GACAAGCCTT  CTCTCCGAAG  AGACCCTGGT  GCTAATGACA  ATTCTGATAG      600
GGACCTCTCA  AAGTATAGCC  CAACTATCAA  TTTGGGCTAG  CCAGAACAGC  AAGGACATCA      660
CACCTACGAT  CAGGAACAGA  TATGCAGGAC  GGTAACCAAT  ACCCACCATC  CAGAAAAGTA      720
AATACGGTAC  CAGAACTGCC  AGATCTGTAA  ACTGTTCCTG  CCATAGCCCG  GCTTAAACAA      780
ACAAACAAAC  ACAAAACTCA  CAAGCACCAC  ACCAAGGGAT  ACAACTTCGA  CCCAGAAGCC      840
ACGGATGCCC  TGGATGATGG  CGCTTCTGTG  CTCTAGATGC  ACCTTCCGCC  GCTGACTGGT      900
CTTATGTTTC  AGGCGAGCAT  GCGCCTTTCG  GCTTCTTAT   TCACGGGCTC  CAGCTCCAGC      960
TGCAGGGCCG  CCAGCGCTCC  AGTGCAGGCC  GGTCACTCAG  GGCTCCGGGC  CTTGGATGGT     1020
CGTGGACATG  CTCCTCCGAG  GACACCTGCT  CCTGCTCCTC  GTATGCCACC  ACCTCCACCT     1080
CCTCCATGAC  GTCCAACACC  AGCAGCTGGA  ACTCCTGCCC  GAGTCCCGCC  ACCTCTCCCT     1140
CCTCCACAGC  CGCACCTTCC  TCCACTGCCT  CCACCCAGAA  GAGGGCGGCC  TCCTCGCCTG     1200
GCGCACCACC  TGCGGCCTGC  ATCGCCTCTG  CCGCCCCAC   CGGACTGGAA  GGCCAGGGCC     1260
CCTCCCTCAT  GAAGACCCGG  GCTCACAACT  AAGATCCAGG  ATCCCGGAGT  CCTGCCGCCT     1320
TCCTCTGGCC  CCGTCTCACT  CTCCATGGTA  TTCTCGCCGA  AGCCGGAAC   TGCAAACAAG     1380
CTGGACGCTA  GAGCACGGCA  GACGGCCCTC  ACGGCCCGCC  GGCGCAGTCT  ACGTGGTCCT     1440
ACTCCCGACG  GTTACTGGGC  AAGAGCCAGG  GAACGGCGAA  AGGGAGAGAC  GCATGCGCAG     1500
AACCCTCTGC  CACCAGGCCG  CCTACTATGG  CGACGGGAAG  GGGCTGAACT  CTCCACCCTG     1560
ACCTCCTGAC  CTCATCCCAG  AACCAATCAA  ATGGAGTCTA  AAGCGGTTCG  CTCCTGGACA     1620
CGCCCCTTGG  AATCCTGGGC  CCTCTTGCCA  CCTGTGACAG  GCGCCAATGT  TGGCCCAGCG     1680
CAAAGTGGGC  GTGGCATGCA  AGCCTTTTGC  CTGCCTAGCA  GTGCAGCCGC  GCCCGAGCAG     1740
CGACTGGGAG  GCCAGGGCCA  CCTGAAGCTG  CAACAGTCCT  CAAGCTTGAA  GTTGCCCCTG     1800
GGGCAGCGCG  CCCGTGTGCT  CAGGGACACA  CTCAGGAAGA  CAGGGTTCCT  GGGTACCTCA     1860
GGGACAGAGT  TGCTCTCCTC  CGATCCAAAC  CGCAAGCCAC  GGGGTGGGGT  GGGGGGAGTA     1920
GGAGGGAGGC  GGGCAGGGTA  GGGGGGTTTG  GGGGAGGAGT  GCGCGGTGGA  GGGGGATGGG     1980
GAAGCGGGGC  GGGGCGGTGG  GGGCGGGCTT  ACGCGACCTC  ACCCATGTGC  ACCTGCTGCA     2040
GAGTCATGGC  TAAACTTGTG  CCTTAGGTTG  AGCAGTTGTC  AGGAATGCAG  CCCTCCTCTG     2100
AGGAAGATGC  AGAGCACTTT  CCTCGGCTAG  CTGTCCAAGC  CCCACGATGC  AGCCGCAAGC     2160
CCAACCAGCC  TGGAGCCCCT  GGCTACGATC  TGTCAGCCCT  CGGCTTTCCC  CCGGCCCGTG     2220
GTTAGGGCAG  GCGCCACGTA  GCTAAGGATG  TGCGCCTGCA  GATGCACTTG  CCAGAGGCAG     2280
```

| | | | | | | |
|---|---|---|---|---|---|---|
| AGCTATTCCT | GCAAGTGTTT | CAAGTGGACC | AAAGTGCTCC | TCCTGACCAT | TAGTTACTCC | 2340 |
| TACGTCCGGG | CCGCCTAGCT | CAGGTGGGCA | CACTCAGGTT | AAGTGCCTGG | ACAGTTTCCA | 2400 |
| CTGCTCACGC | TCTTTCTCCT | AGGATGTCTG | CTGTTTCACA | CTGAGCACCT | ACCTCCCTTA | 2460 |
| GTCCTGACAC | ACTCACAGGG | CCACCACAGC | CCACCCCACC | CCCCACACCC | CCCCACAAAC | 2520 |
| ACACACAAAC | ACGTGACACA | AGTACACACA | TGCGTGCAAC | ACACAGAGCC | ACAAATGCCA | 2580 |
| ACAGGTGTTT | CAGAGACTGA | AGAACCAGTG | GTTCGCATGA | AATGATAGAT | GTCTTTATTT | 2640 |
| CTAACGGGAA | AATGTTCATT | CTGATCTTCA | GATGTGAAAT | ATAGAGAAGT | CCATCTTCCA | 2700 |
| TGAGGGAGAA | TCATGCCTAG | ATTTGGATAC | AGGAAGTATA | GAGGAACTCC | TTATTTCATG | 2760 |
| GTGGACAGTC | CTTGATTTAT | GCATGAGAAA | TACAAGGAGT | TAAGTATTTC | ACGAAGAAAC | 2820 |
| AGTGGTGCCC | AGAATTTCAT | TTATGAAATA | GAGATAATTC | CAATTCCATA | TTGGTTCACC | 2880 |
| AGATCTTAAT | TTCACACTTC | ATGTCAGTAA | ACTTTCATTG | AGATCTTCAT | ATACGAAATG | 2940 |
| TATACAATTT | CAGGATTCAA | GAAGGGAATT | GTAGGCTCAA | CTTTTCATAT | GTAAAATATA | 3000 |
| TAGAATTCCA | AATTTCATGC | CGGCAAATAA | CACGTGCACC | CATGATTCAT | ATTACATATA | 3060 |
| GAGAATTC | | | | | | 3068 |

( 2 ) INFORMATION FOR SEQ ID NO:4:

( i ) SEQUENCE CHARACTERISTICS:
        ( A ) LENGTH: 2104 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

| | | | | | | |
|---|---|---|---|---|---|---|
| GAATTCACTG | CAAAGGAAAA | ATAAAAAGCA | TCAGCTGCAT | GCGTGCGTGT | ATTGTTTGGG | 60 |
| CAGGTCCTCA | GGACAAACAC | TTCAGCTGCA | TGTACGAGTG | TCAGTTCACC | GCGTGGGAAT | 120 |
| TACCAGTCTG | TGGAGATTCA | TAGAGGGGGC | TAAGTCGTAT | GTTGGGGTTG | TGTCAGGGGG | 180 |
| TGACGTTCTT | CCTGTGGGGT | GGGGGTTGGG | GAGGACGGAG | AAGGAAGATG | AGGGGCCTAT | 240 |
| TGACTGTGGG | TCTGGCAATT | TTACAAGGGA | AATGTGGCTG | TTCGTGGAAA | GGGTCTGGTG | 300 |
| AACAAGGGCC | AGAGATTGAA | ACAGTGGAAT | GCAATTCTGT | TGGAAGGTGG | TGGCCCAGGT | 360 |
| ATCTTCTCTG | TTGCCTATCA | TCAGACACTT | TAATAAGGGT | ACAGAACAAA | GGAAAAGCCT | 420 |
| TATCATTGAA | CTCGCTATGA | ACCTCGAAGG | CCACATGTGT | ATGAGTGTGT | ATATGAGTGC | 480 |
| ACGGTCAGCT | TTGCTGAGAG | TCTGCTTCCC | AGAGCTAGGG | TTCCAGGTAA | CATCTTAGGG | 540 |
| CATTGTGTAT | AAGGTATATG | GAGGGGGGCT | GTGGCCTAGG | GAGAAAGTGA | GGGGTGGGAA | 600 |
| GGCAGTGAGG | ATACTAGTTT | CTGGCAAAGG | TGACCAGGGG | AAAAGAGAAA | TTGCAAGGAA | 660 |
| TCAGATAAAG | GAAAACAGAT | CCCGTCGTAG | ATGTTAGAGC | TCATGTGAAC | TCTGTTATTT | 720 |
| TTTCCAAGAA | CTCAGCTTCG | GTATAGCGTG | TCCAGGGGCA | GAAGTGAGGG | GAAAGAGGCT | 780 |
| GTTAGGGTGA | GCCTATGCAG | CCATGTGGTC | TGTGTCCCAT | GCTGCTGCTG | CTGCTGCTGC | 840 |
| TGCTGCAGCT | CAGGGGTCAA | TATCCCTTTT | TCCAGGAAGG | CTTAAGGTCT | TTGCCCAAGG | 900 |
| CCCTCTGTCA | GGCCAAGCTG | TAGAAAAAGC | ATTTTTTCTC | ACCAGCCCTC | TGGTGACAGT | 960 |
| TTCTCTTCCT | TGTGGAATGG | CTCAGCACAG | AATGTTTTCA | ACCACAAAGG | AGCTGTCCTT | 1020 |
| CATCTAGGGC | TTTGCACTAC | TGTGTGGGCC | AAGGGCAGTG | GGAACAGCTG | GAGCACATGG | 1080 |
| AGCTCACTGA | GGGACTGGTC | GGCACTTAGG | GTGGTCCTTC | TGAAGTAGAT | GACTGCTTTC | 1140 |

-continued

| TGGAATCGCG | TCCACCTCTG | GATTGAGCAA | AAGACAGACT | GGCACAAATG | GAGTAGGCAG | 1200 |
| AGTTCAACGT | CTGTCCCCCT | ACTGTTGTCC | TCTCATCCCA | GATAGAAGGG | CTCCACCGTG | 1260 |
| GGCATGCCTG | AGGGTGATGT | CCCACATGAA | GTTCTGTCTC | GCATGAAGTT | CTCACTCTAC | 1320 |
| AACTTTTCTC | CCTGAAGCAG | CATCTCTTTT | GAGGGCAAAG | GGTAAAGTTC | ACAGGTTTTA | 1380 |
| TGGATGTCCT | CTTCACGGTG | CCCTGCATGA | GATCTCCTGC | CCAGGGCCAG | CTTTTGCATT | 1440 |
| TGACCATGTA | CACCCCAGCT | TTGCCCCTTC | TCCAGAGACG | CATCTACAGC | GCTAGAAGGC | 1500 |
| AAGGCTTGGC | CGTCTCTGGG | TGCTTTCTGA | ACAAGCAGCC | AGGAGACAC | TGGAAACATG | 1560 |
| TCTTCTTACT | TTCTGAATCT | GTCAACGTCC | AAGAATCCGT | GGGGCTCCGG | CAGGCTGGTA | 1620 |
| CCTGTCTTTC | CCAGTCCTAG | TTCAAAACAA | AACAAAGCAG | AAACTATGGT | GTGATAACTC | 1680 |
| GACAGCGGGT | GTGAGATGGC | ATACTGGGGC | ATGGTTTTCG | GACCTTAGA | CTGGGCTCAT | 1740 |
| TCTAGGGACT | GCATGGCATT | TACCCACATT | CAGAAGTTTC | CGTAAGGCAT | TGCAAAGAAG | 1800 |
| TTAAAGACAA | GAAAAGTTTA | GGACAGGGTC | CCCCAGTGCC | TAATATTTCC | TGCCAGTGCT | 1860 |
| TCAGGACCAG | GGTTGGCATT | AGCTCTAACC | TGTCCTCGAG | TGGAGTGCAG | AGATAGTCTT | 1920 |
| CGTTGACTGG | ATGGTCATCC | TCTGGAGACT | TGCCGTGACT | TGTGTCCCAG | GCTCTCTAGG | 1980 |
| GCTTTCACTT | GGGCCCTAAA | GGCTAGGTGC | TCTTAGAGTT | GACTGCACAC | TTGGATGTGT | 2040 |
| CGTGTAAGGT | TTTCTTCCGC | CGAATATCGA | TGCGTGTGAG | ACTCGCCGGT | TTAGTGATGA | 2100 |
| ATTC | | | | | | 2104 |

( 2 ) INFORMATION FOR SEQ ID NO:5:

( i ) SEQUENCE CHARACTERISTICS:
        ( A ) LENGTH: 305 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

| GATCTGTTGG | AGGTTCAGGT | ATTGAGATTT | GTTAGAAACC | ATGCTATTGC | TAAAATGAAA | 60 |
| CCAATGTCGC | CGATGCGGTT | ATATAAGATT | GCTTGTAGGC | TGCTGTGTTT | GCATCTGTCG | 120 |
| TCCGTATCAT | CATCCGATGA | GTAGATGATA | TGATTCCGAC | GCCTTCTCAG | CCAATGAATA | 180 |
| GCTGGAAGAG | GTTGTTTGCG | GTTACAAGGA | TGAGCATAGT | ATGAGGAATA | GGAGTAGGTA | 240 |
| TTTGAAGAAT | TTGTTAATAT | TGGGGTCTGA | GTGTATATAT | CATATTGAGA | ATTCTATAAT | 300 |
| AGATC | | | | | | 305 |

( 2 ) INFORMATION FOR SEQ ID NO:6:

( i ) SEQUENCE CHARACTERISTICS:
        ( A ) LENGTH: 373 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

| GATCAAGCTA | AAGAAATCTT | CCTTATTTGA | AAGGCCGAAA | GACAAGCAAG | CAAGCAAACA | 60 |
| AAACAAAAAC | CCACATCCCT | AAATCAAACT | ATTGCCCTAG | CGCAAAACAG | AAGCAGATTT | 120 |
| CACAGCCCGA | GGTCAGCCTA | GCAGGCTTGA | GAAAGAATGT | TTAATTATAA | ACTAAAACAA | 180 |
| CAGGATTCCA | AAGGATAAGC | GGTCCTGCAG | GGAAATCTAT | TCGTTTTGAT | TTTTTCTCTC | 240 |

| TCAGTGTCCT | GTCAAATAGA | AGCCACTTGT | AGAATCCGCT | AAACATTGTT | CTGCATTAGA | 300 |
| AATATTGCAT | ATTGAGCGCA | CACACACACA | CCACACACAT | ATACAGAGGA | AAGACTTACT | 360 |
| CTTGGGAATG | ATC | | | | | 373 |

( 2 ) INFORMATION FOR SEQ ID NO:7:

( i ) SEQUENCE CHARACTERISTICS:
        ( A ) LENGTH: 241 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

| GATCAGTGCA | TAATCAGCCA | CATAATCAGT | GCATGATAGC | CACCTGACCA | GTGCATGATC | 60 |
| CATCTTTTGT | TTTCTCCTCT | GAGGAAGAAG | CCCAAGTTGC | TAAGCACTCT | ATTTCCGTTT | 120 |
| CTTGGCTCCT | CCTCCTCCAA | CTTTAACAGT | TTGCTTAATC | AATCCCCATT | TGCTCCGAAG | 180 |
| TCTAGTTCTG | CCACTTCAGC | TTGCTCCATC | TTCTCTGTTG | ACCCACATGC | ATATTAAGAT | 240 |
| C | | | | | | 241 |

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| TGGACATTGC | CACAACCATT | 20 |

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| GCTGAATGCA | CTGAGAGAGA | 20 |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

| GCCCAAGTTG | CTAAGCACTC | 20 |

( 2 ) INFORMATION FOR SEQ ID NO:11:

( i ) SEQUENCE CHARACTERISTICS:
        ( A ) LENGTH: 20 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:11:

GCAGAACTAG ACTTCGGAGC    20

(2) INFORMATION FOR SEQ ID NO:12:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:12:

GAGCTCGGTC CTGTAGACTG    20

(2) INFORMATION FOR SEQ ID NO:13:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:13:

TGAACTGTGG TGCTTGGACA    20

(2) INFORMATION FOR SEQ ID NO:14:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:14:

TTACCAGTCT GTGGAGATTC    20

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:15:

CCTAAGATGT TACCTGGAAC    20

(2) INFORMATION FOR SEQ ID NO:16:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

( x i ) SEQUENCE DESCRIPTION: SEQ ID NO:16:

TGTCAACGTC CAAGAATCCG                                                                                               20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CTCGAGGACA GGTTAGAGCT                                                                                               20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GTGATAACTG CGACAGCGGT                                                                                               20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TCATCACTAA ACCGGCGAGT                                                                                               20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AAACCAATGT CGCCGATGCG                                                                                               20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CTCAGACCCC AATATTAACA                                                                                               20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TGATATGATT CCGACGCCTT     20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CAAATACCTA CTCCTATTCC     20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CCACATCCCT AAATCAAACT     20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CTACAAGTGG CTTCTATTTG     20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

GCAGATTTCA CAGCCCGAGG     20

(2) INFORMATION FOR SEQ ID NO:27:

(i) SEQUENCE CHARACTERISTICS:
        (A) LENGTH: 20 base pairs
        (B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:27:

TTCCCTGCAG GACCGCTTAT                                                               20